(12) United States Patent
Blumberg

(10) Patent No.: US 7,382,231 B2
(45) Date of Patent: Jun. 3, 2008

(54) ELECTRONIC MEMORY PAD

(76) Inventor: Marjorie Blumberg, 9722 Whitley Park Pl., Bethesda, MD (US) 20814

( * ) Notice: Subject to any disclaimer, the term of this patent is extended or adjusted under 35 U.S.C. 154(b) by 163 days.

(21) Appl. No.: 11/056,393

(22) Filed: Feb. 14, 2005

(65) Prior Publication Data

US 2005/0190655 A1 Sep. 1, 2005

Related U.S. Application Data

(60) Provisional application No. 60/543,658, filed on Feb. 12, 2004.

(51) Int. Cl.
*G08B 1/00* (2006.01)
(52) U.S. Cl. .............. 340/309.15; 340/539.11; 340/539.12; 340/309.7; 340/521
(58) Field of Classification Search .......... 340/309.15, 340/539.11, 539.12, 309.16, 309.7, 321, 691.6
See application file for complete search history.

(56) References Cited

U.S. PATENT DOCUMENTS

| | | | |
|---|---|---|---|
| 3,999,050 A | 12/1976 | Pitroda | |
| 4,385,291 A | 5/1983 | Piguet | |
| 4,751,668 A | 6/1988 | Aihara | |
| 4,847,760 A | 7/1989 | Yagi | |
| 5,124,960 A | 6/1992 | Miller et al. | |
| 5,457,476 A | 10/1995 | Jenson | |
| 5,696,496 A * | 12/1997 | Kumar | 340/825.25 |
| 5,929,747 A | 7/1999 | Rosenblatt et al. | |
| 6,198,695 B1 * | 3/2001 | Kirton et al. | 368/10 |
| 6,484,033 B2 * | 11/2002 | Murray | 455/456.3 |
| 6,553,267 B1 | 4/2003 | Watari | |
| 2003/0058225 A1 | 3/2003 | Kusuda et al. | |
| 2003/0103672 A1 | 6/2003 | Lapstun et al. | |
| 2003/0212579 A1 | 11/2003 | Brown et al. | |

* cited by examiner

*Primary Examiner*—Daryl C Pope
(74) *Attorney, Agent, or Firm*—Arent Fox LLP.

(57) ABSTRACT

An electronic memory device in which a user can customize the keys on a keypad, record the occurrence of and information related to an unscheduled medical event or a scheduled medical event, for example, the taking of medication, and set a predetermined time interval between scheduled medical events. The keys are customizable so that the user can identify specific medications or specific symptoms. The device can be in the form of a personal digital assistant-based memory pad having icon keys so that the user can easily enter data, and an electronic pen for activating the on-screen icon keys.

27 Claims, 8 Drawing Sheets

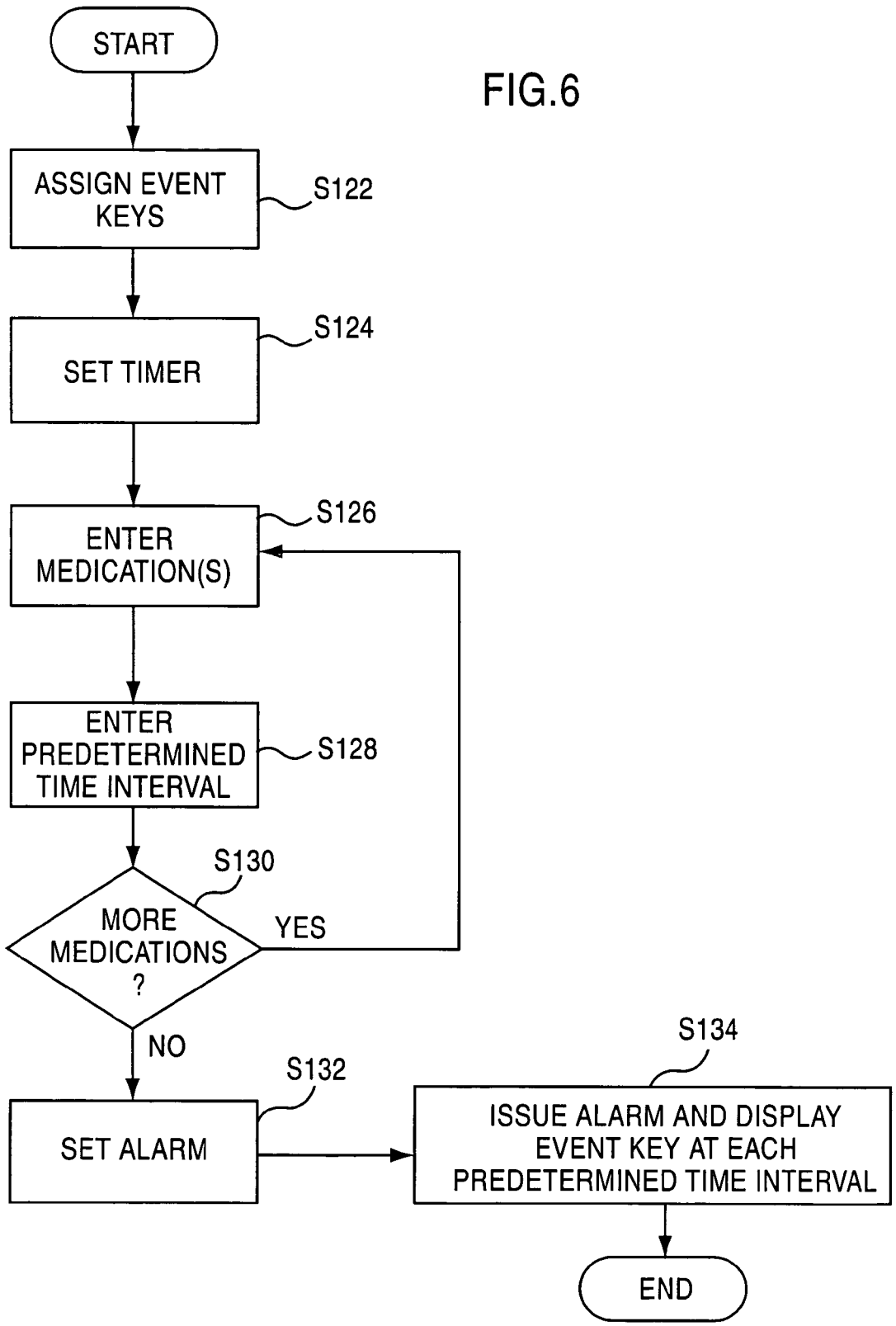

ELECTRONIC MEMORY PAD

RELATED APPLICATIONS

This application claims priority to Applicant's co-pending U.S. Provisional Application Ser. No. 60/543,658 entitled "FORGET-ME-NOT MEMORY PAD" filed Feb. 12, 2004. The entirety of this prior patent application is incorporated herein by reference.

BACKGROUND OF INVENTION

1. Field of the Invention

The present invention relates to an electronic memory pad and complementary features of the electronic memory pad. More specifically, the present invention relates to a customizable electronic memory pad that can (1) record and play back information related to multiple unscheduled events occurring at varying time intervals and medical events (for example, taking of medication) occurring at scheduled and/or varying time intervals, and (2) remind a user of a required time for a single scheduled event or a required time interval between multiple scheduled events.

2. Description of the Related Art

Individuals who wish to record the occurrence of physical symptoms that occur at different times of the day or the required time intervals between different medications have had to rely on their memory or record the event with pen and paper. Such information would generally include the date and time that the physical symptom was felt or the time intervals between different medications. This type of recording is difficult when there are a number of different physical symptoms occurring at irregular intervals or when the individual seeks to record multiple events at night.

Individuals who are taking medications often record when a medication should be taken, but have a tendency not to record when a particular medication can be taken in relation to another medication. Such lack of recordation can result in adverse drug interaction such as one drug reducing, neutralizing, or increasing the effects of another; two similar drugs causing an effect much greater than would normally be expected; and two drugs taken together causing a new, unexpected, and unhealthy reaction. Other adverse drug interactions can include cardiovascular events, seizures, and gastric irritation and erosion of the protective lining of the stomach. Even foods and non-prescription medications can react with prescription drugs. For example, salt substitutes can interact with some diuretics causing nausea, vomiting, and even cardiac arrest; decongestants can interact with diuretics increasing blood pressure; antacids can slow the absorption of blood-thinning drugs; and aspirin can increase the effects of blood-thinning drugs and could make any bleeding difficult to stop. As a result, individuals taking more than one drug must carefully follow their physician's orders for the administration of the medications. However, if an individual is receiving medications from different physicians, the orders, even if followed correctly, may be hazardous with respect to other medications. This scenario becomes particularly important for seniors or the elderly where the likelihood of needing to take several medications increases with age. As such, the risk of a drug interaction also increases. Forty percent of individuals who have experienced an adverse drug interaction are more than 60 years old.

Recently, advances in the field of electronics have yielded the personal digital assistant (PDA) handheld devices designed as personal organizers for storing tasks and appointments and for performing calculations. However, the keypad for inputting information is pre-designated from the manufacturer with an arrangement that coincides with conventional lettering and numbering systems.

The inventor of the present invention has developed a recording device that allows a user to customize the keypad for the user's specific circumstances.

SUMMARY OF THE INVENTION

In the health care arena, the electronic memory pad of the present invention addresses a user's need to accurately record and document health- or medical-related events in real time. Also, the electronic memory pad can be programmed to remind the user to wait a required time interval between taking particular medications. Medical-related events, hereinafter "medical events," can include, for example, symptoms from an illness or the taking of medications.

The electronic memory pad of the present invention can record the circumstances surrounding a user's discomfort based on a real-time input of the symptoms suffered by the user, and can remind the user of the required time interval between taking different medications. The present invention allows a user to record one or more medical events electronically, and without the use of pencil and paper. In operation, the device of the present invention records, for example, what the symptom was, when the symptom occurred, how severe the symptom was, and how long the symptom lasted. The device of the present invention also allows recording when a particular medication was taken and how long the user must wait between taking particular medications, with an integrated clock, timer, and alarm.

Many individuals take antacids in addition to regular prescription medications; however, as discussed above, antacids and some prescription medications are incompatible; as such, a one-hour to two-hour waiting-time interval between ingesting the prescription medication and the antacid or the antacid and the prescription medicine, respectively, is required. With the electronic memory pad of the present invention, a user can record the date and time that an antacid is being taken and program when the non-compatible medication can be taken, and vice versa. Then, before the user takes the non-compatible medication, the user can check a countdown timer to determine whether the non-compatible medication can be taken. When the required time has elapsed, the device will remind the user to take the next medication by emitting a chime or other audible signal.

The device can be a PDA-based memory pad having icon keys so that the user can easily enter data with, for example, a stylus pen. In one embodiment of the present invention, the device can store information related to the time a medical event occurred, such as physical pain or a symptom, and store the duration of the medical event. The device can also be programmed to store information related to different medications, including the required time interval between taking different medications, and sound an alarm to remind the user of the required time period between taking particular medications.

The present invention also includes labels that can be pre-printed with common ailments or medications, for example, or blank customizable labels, so that the user can print their particular medical events. The labels can be assigned to specific keys on the keypad to represent the different medical events. The labels can be reusable so that the user can customize the keypad of the electronic memory pad as necessary.

In addition, the electronic memory pad can be a hand-held portable device that a user can easily transport on their person, in a briefcase, or in a purse. Portability allows the user to easily take the device to a physician and show the physician a real-time record of the user's symptoms. For example, the device can have hooks for threading a strap or belt so that the user can wear the device on their person. As such, the user does not have to rely on memory to describe to the physician when a particular symptom was felt or a medical event occurred. Also, the physician can more easily discern the circumstances surrounding the ailment based on a clearly recorded-real time entry of the users symptoms.

The device of the present invention also includes a backlight feature for the display screens, so that in a darkened environment, the user would be able to read and record medical events regarding the symptom.

The device of the present invention can also include a voice-activated control system. The voice-activated control system activates a clock such that, at an alarm point, a recorded voice plays back stored information. The stored information is repeatedly played back until the user deactivates the system. The device keeps track of how long the stored information was played back by the voice-activated control system before deactivation. The voice-activated control system can recognize accents and dialects, and can include a language selection feature.

The device of the present invention includes a time-comparison circuit for comparing a present time with an alarm time, and an alarm signal for generating an audible alarm at the alarm time. The alarm can not only remind the user to take a medication, but also can remind the user to take a specific medication in a series of medications. For example, the user can input into the device the different medications and the required or recommended times that these medications must be taken. Each of the medications and their scheduled intake will be stored in the device. When the time-comparison circuit compares the present time to the alarm time for each medication, an alarm will sound. The alarm can have any sound, including various tones, such as a chime, or the alarm can repeat the voice from the voice-activating system repeating the name of the medication to be taken.

It is necessary for an individual to talk with his or her general physician or pharmacist for a detailed prescription of which drugs should be taken first and the time intervals necessary for taking multiple medications. Once this information is inputted into the timing device, the present invention can relieve the user of having to remember the sequence because the timing of each medication can be programmed for regularly scheduled times indefinitely, similar to an alarm clock.

The present invention also includes a method of recording a medical event and a method of scheduling a predetermined time interval between medical events in an electronic memory device. The medical event can include a symptom or the taking of a medication.

The electronic memory device of the present invention allows a user to more accurately discuss with their physician how often a particular medication has been taken, or when and how often the user has been experiencing a particular symptom. The user can refer to the electronic memory pad and accurately answer the physician's questions so that the physician can extract the data regarding the symptoms and their frequency, or timing, or severity, which can lead to a diagnosis of the user's ailment.

As a result of the present invention, when using the electronic memory pad, a patient can have an accurate and real-time record of their symptoms or ailments for analysis by the physician, which can, in turn, improve the physician's ability to make a precise diagnosis and recommendation for treatment.

Additional advantages and novel features of the invention are set forth in the attachments to this summary, and in part will become more apparent to those skilled in the art upon examination of the following or upon learning by practice of the invention.

BRIEF DESCRIPTION OF THE DRAWINGS

The features of the invention will be more readily understood with reference to the following description and the attached drawings, wherein:

FIG. 6 illustrates a flow chart for a method of scheduling a predetermined time interval between a plurality of events in the electronic memory pad according to one embodiment of the present invention.

DETAILED DESCRIPTION OF THE INVENTION

The present invention is directed to an electronic memory device in which a user can customize the keys on a keypad, record the occurrence of, and information related to, an unscheduled medical event or a scheduled medical event, and set a predetermined time interval between scheduled medical events. In one embodiment of the present invention, the event can be a medical event such as a symptom of an illness. Such symptoms for different illnesses may include stomach pain, dizziness, joint pain, back pain, or rash. The device records and plays back information to a user regarding specific medical events so that the user can track symptoms and physical ailments, and a physician playing back the recorded information can have a clear understanding of the user's ailments in order to make a diagnosis.

Figure 1:
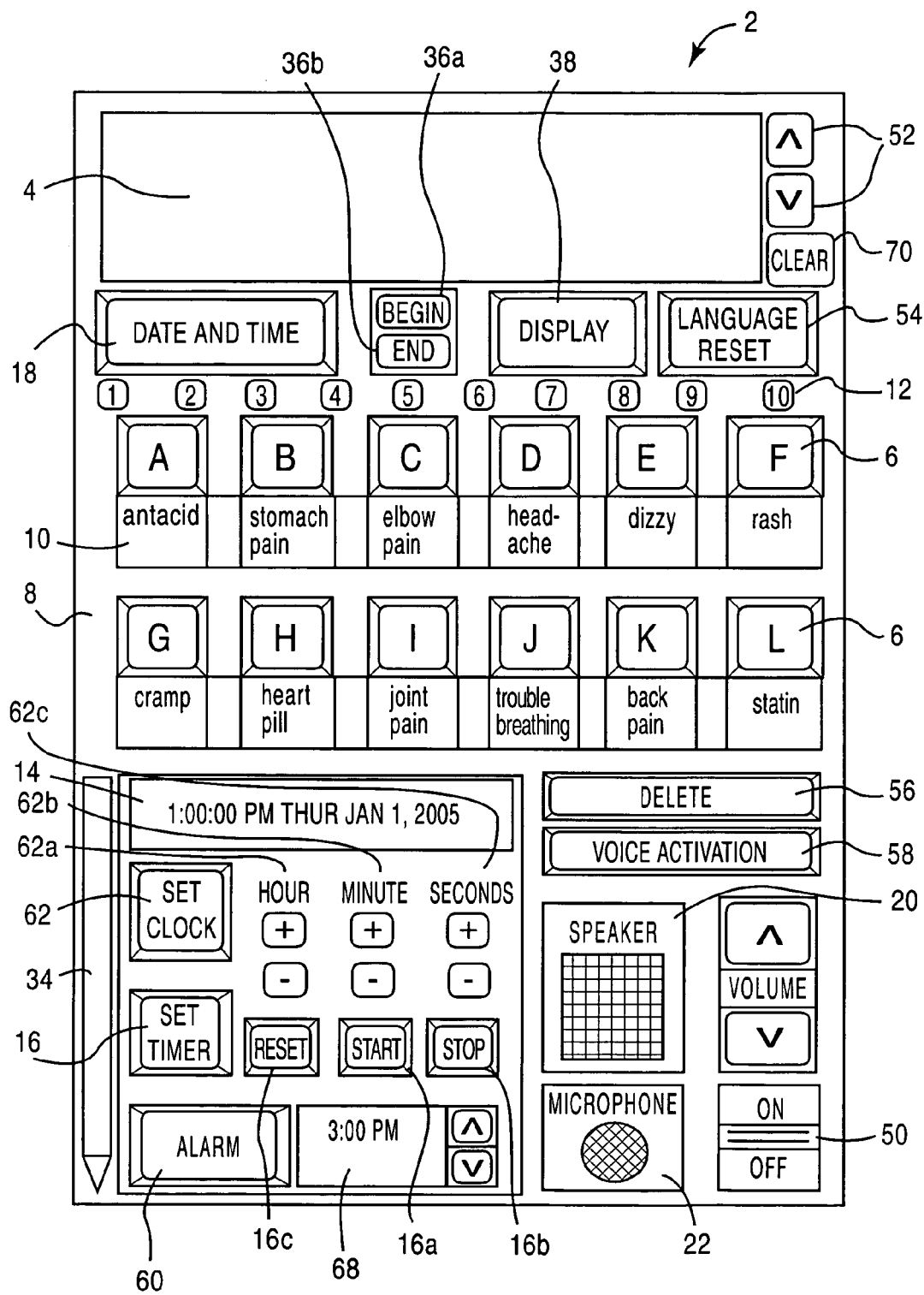
FIG. 1 illustrates a front view of the electronic memory pad according to one embodiment of the present invention.

As shown in FIG. 1, the device 2 of the present invention includes at least one display screen 4, which can be a liquid crystal display (LCD). The display screen 4 displays characters selected by the user from a keypad 8. The present invention can also include a second display screen 14, linked to the first display screen 4. As shown in the embodiment of FIG. 1, the first display screen 4 conveys information regarding symptoms that the user is experiencing and medications that the user is taking. The second display screen 14 conveys current date and time. A DISPLAY key 38 allows a user to display stored information on the display screen 4. The user can scroll through the displayed information with scroll buttons 52. A SET CLOCK key 62 starts a sequence for setting the current date and time. For example, pressing the SET CLOCK key 62 once allows the user to adjust the day and date. Pressing the SET CLOCK key twice allows the user to change the time. An HOUR key 62a, MINUTE key 62b, and SECONDS key 62c can adjust the time displayed on the second display screen 14, and also are used to set the day, month, and year. The time in the second display screen 14 can also display seconds.

In an embodiment of the present invention, the keypad 8 has a plurality of event keys 6 that can be customized to designate events to be recorded in the device 2, and to be displayed on the first display screen 4. Although FIG. 1 illustrates twelve event keys labeled A to L, the present invention can have more or fewer event keys, and is, therefore, not limited to the number of event keys or rating keys shown in the figures. The event keys 6 can be interchangeably assigned to an event. For example, if the user is experiencing symptoms related to a cold, the user can customize all or some of the event keys on keypad 8 so that the event keys 6 specify different cold symptoms. At another time, if the user is experiencing symptoms related to an unknown cause, the user can describe the symptoms and assign the symptoms to the event keys 6 on the keypad 8. Thus, as the user experiences different or repeating symptoms, the user can change the assignment of the event keys 6.

Figure 2:
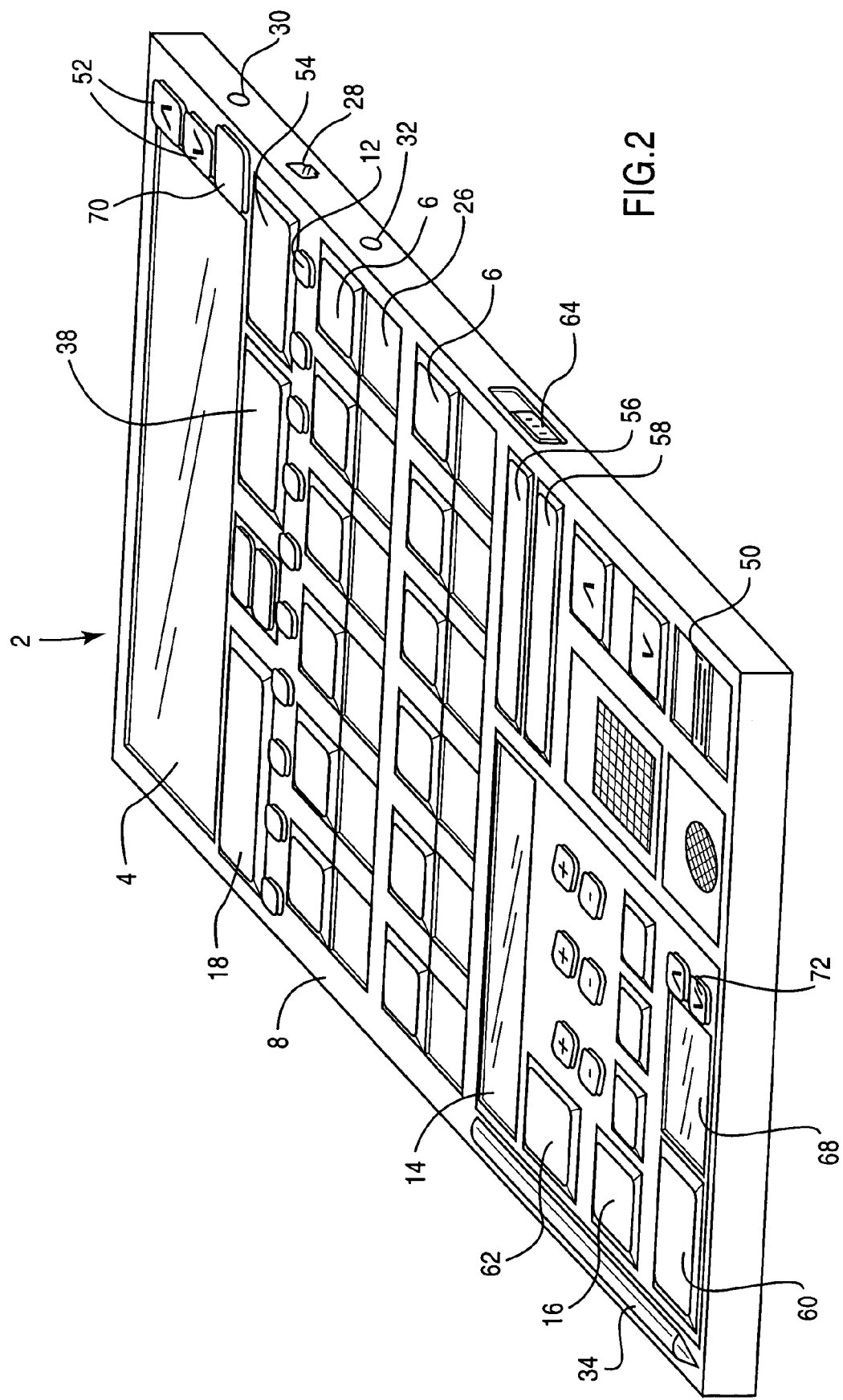
FIG. 2 illustrates a front perspective view of the electronic memory pad according to one embodiment of the present invention.

In order to customize the event keys 6 of the keypad 8, the present invention includes a plurality of event key identifiers 10. The event key identifiers 10 can include labels, such as, for example, adhesive labels pre-printed with common ailments. The event key identifiers 10 can also be blank adhesive labels that the user can write on, describing symptoms. The labels can then be affixed in an event key assignment zone 26, shown in FIG. 2, proximal to the event key to represent the symptom.

The present invention also includes a plurality of rating keys 12 for recording and rating each of the events. The rating keys 12 can indicate the severity of the symptom that the user is experiencing. For example, as shown in FIG. 1, the rating keys 12 can be numbered from 1 to 10 with 1 being the least severe to 10 being the most severe.

The device of the present invention also includes BEGIN and END keys 36a, 36b that allow the user to record the duration of the medical event. For example, as discussed below with respect to FIG. 5A, by pressing the BEGIN key 36a at the beginning of a symptom, and then pressing the END key 36b at the time the symptom ends, the user can record the beginning and end times of the symptom and calculate how long the symptom lasted.

If a second symptom occurs concurrently with the first symptom that is being recorded, as discussed below with respect to FIG. 5B, the user can input the second symptom, press the DATE AND TIME key, then the BEGIN key 36a to record the start of the symptom. If there are no other symptoms at S121 being recorded the process continues at S112.

When the user inputs the symptoms into the device, through the event keys 6, a memory circuit records the medical events for storage and play back. The memory circuit can be similar to a memory circuit in a PDA, which features are incorporated herein by reference. If the user wishes to delete a stored entry for a particular event key 6, user can press the DELETE key 56. In one embodiment of the present invention, the user can activate the DELETE key 56 by pressing the key in a particular pattern such as, for example, pressing DELETE key 56 twice or pressing the DELETE key 56 for several seconds to prevent accidental deletion of the stored entry. In another embodiment of the present invention, the user can delete the contents stored under a particular event key 6 by pressing the DELETE key 56 of the particular event key and the DELETE key again. Deleting the stored information for one event key at a time allows the user to discard only information related to symptoms that are no longer at issue. If the user presses an event key 6 by mistake, pressing the CLEAR key 70 deletes activation. If the user presses an event key 6 by mistake followed by the DATE AND TIME key, the user can press the CLEAR key 70, which will delete just that last entry.

If the user wishes to delete all stored entries in a particular event key 6, the user can activate the event key 6, the activate the DELETE key 56 by pressing the key in a particular pattern such as, for example, pressing the DELETE key 56 twice or pressing the DELETE key 56 for several seconds to prevent accidental deletion of the stored entries. Deleting the stored information for one event key at a time allows the user to discard only information related to symptoms that are no longer at issue.

If the user wishes to delete a stored entry, the user can scroll through the display screen 4 with the scroll buttons 52 to highlight the stored entry and press the DELETE key 56.

The device 2 can include a stylus pen 34, so that the user can more easily select the event key 6 or rating key 12. The stylus pen 34 can be tethered to the device to prevent misplacement.

The device 2 of the present invention also allows a user to schedule a predetermined time interval between medical events. Such medical events can include the taking of medications. For example, some medications taken within a certain amount of time of each other can cause the user to suffer an adverse reaction. The device 2 of the present invention allows a user to schedule the required time interval between taking different medications and thereby reduce the likelihood of an adverse reaction.

In order to customize the event keys 6 on the keypad 8 and space the intake of different medications, the plurality of event key identifiers 10 can be designated with common medications. For example, as shown in FIG. 1, event key "A" can be designated as an antacid and event key "H" can be designated as a heart pill. The event key identifiers 10 can also include blank adhesive labels for the user to write his or her specific medication. The labels can then be affixed onto an event key assignment zone 26 to represent the medication.

Figure 5A:
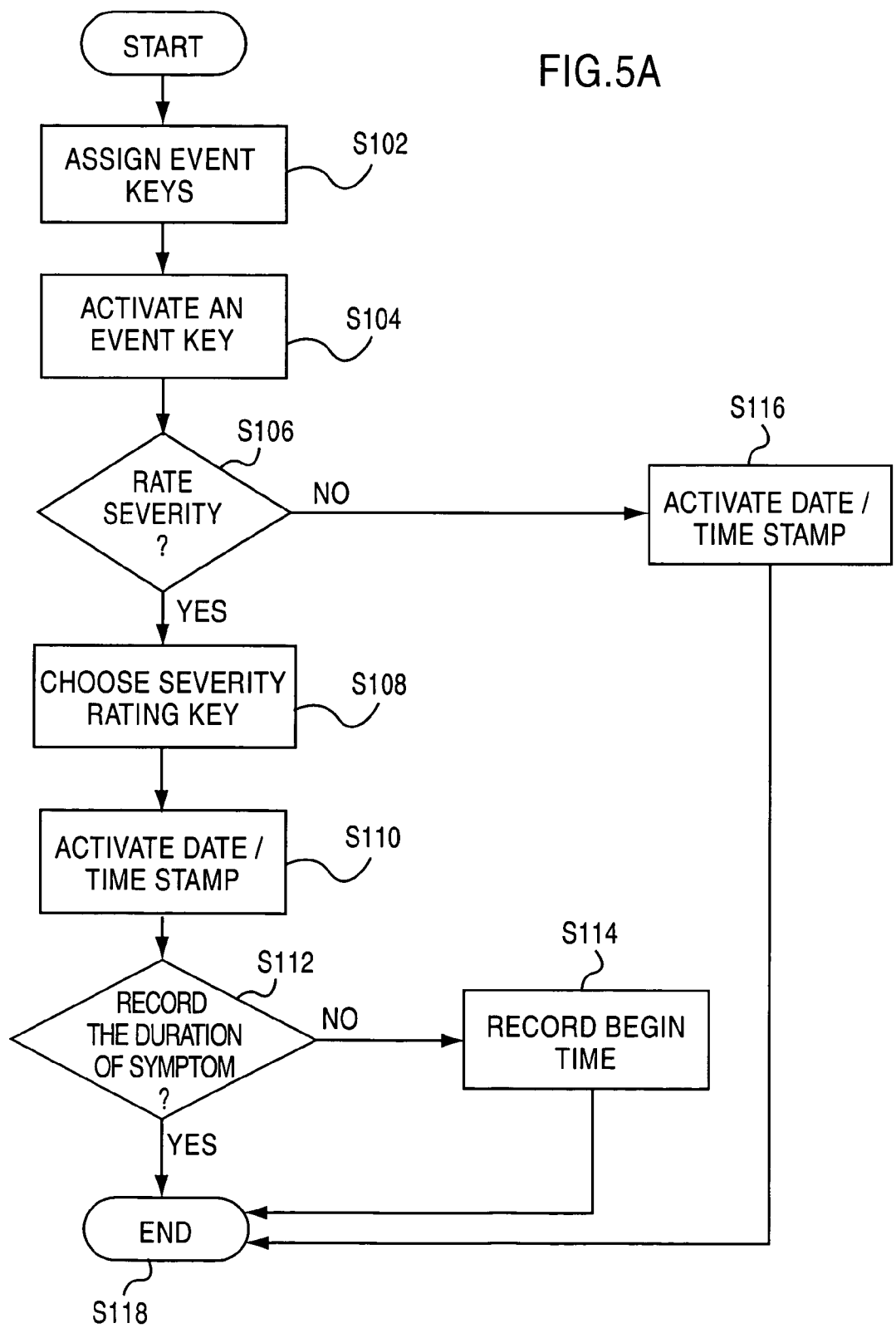
FIGS. 5A and 5B illustrate flow charts for a method of recording an unscheduled event in the electronic memory pad according to one embodiment of the present invention.

The present invention also includes a method of recording a medical event in the electronic memory device 2. As shown in FIG. 5A, the method includes at step S102 assigning the plurality of event keys 6 with event key identifiers 10; activating one of the plurality of event keys 6 to display an event on the display screen 4 at step S104; and at step S116, activating the DATE AND TIME key 18 to display a current date and time of the medical event on the display screen 4. The device 2 allows the user to record the duration of the event at step S112. The step of assigning event keys S102 includes assigning event key identifiers 10, such as the customized labels, to the plurality of event keys 6. The customized labels can be pre-printed with different symptoms, or custom-written by the user.

The method also includes rating the medical event with a severity scale from 1 to 10, where 1 is the least severe, or causes the least discomfort, while 10 is the most severe or causes the most discomfort. For example, the user can first select the event key to be recorded and the severity of the event. To store the information related to a medical event in the device 2, the user can press the DATE AND TIME key 18.

The method of recording a medical event also can include recording the onset of the event using the BEGIN key 36a, and the END key 36b to record that the event has concluded. If no other events have been monitored between the BEGIN and END of the one event, a user can simply press the END key 36b to mark the end of the event. However, if a second event has been entered after the first, then the user can press the first event key being recorded, and the DATE AND TIME key, followed by the END key 36b.

The device of the present invention also provides a method of scheduling a predetermined time interval between medical events. As shown in FIG. 6, the method includes assigning different medical events to different event keys 6. Assigning the event to the event keys 6 includes labeling the event keys with the event key identifiers 10, pre-printed or user-customized labels that identify the different medications that the user is taking. As such, each event key 6 could represent a different medication.

In order to schedule a predetermined time interval between different medications, the user can store the predetermined time intervals between the different medications in the device. Then, the user can set the timer 16, activating the time-comparison circuit for comparing a present time with an alarm time. An alarm signal generates an audible alarm at the alarm time. The audible alarm can be emitted from a speaker 20 located on the front face of the device, for example. The device issues an alarm after each of the predetermined time intervals, and displays the event key 6 in the display screen 4 so that the user knows which medication to take at the alarm time. The alarm can not only remind the user to take a medication, but also can remind the user to take a specific medication in a series of medications. For example, the user can enter the event keys representing different medications into the device 2 and the required or recommended times that these medications must be taken. Each of the medications and their scheduled intake times will be stored in the device. When the time-comparison circuit compares the present time to the alarm time, an alarm will sound at the alarm point for each medication.

The alarm can have any sound including various tones, such as a chime, with the letter of the event blinking in the display screen 4, or the alarm can be a voice or a chime from a voice-activating system. At the alarm time, the audible chime can continue and the letter designating the event can continue to blink, or the voice from the voice-activating system can repeat the name of the medication to be taken—until deactivated by the user. The user can deactivate both the chime and voice alarm by pressing the ALARM key 60.

The device 2 of the present invention can also include a voice-activated control system. The voice-activated control system activates a clock such that at the alarm point, a recorded voice plays back stored information. The stored information is repeatedly played back until the user deactivates the system. The device 2 keeps track of how long the stored information was being played back by the voice-activated control system. Therefore, if the user is away from the device and returns after the alarm point, the user can know how much time has passed since the medication should have been taken.

In another embodiment of the present invention, pressing the VOICE ACTIVATION key 58 can activate the voice-activation feature. The user can then issue a command, "SET TIMER ONE MINUTE", the device can audibly play back a chime to indicate that the command was received. Then at the end of one minute the device will chime twice. The voice activation system can continue to receive voice commands without having to press the VOICE ACTIVATION key 58 a second time. By pressing the VOICE ACTIVATION key 58 a second time, closes the voice activation loop so that the voice activation key will stop receiving further voice commands. The voice activation system can include the voice activation circuit of any hands-free voice activation system as discussed below.

Activating the time-comparison circuit can include voice-activating a start and stop time of the time-comparison circuit with the voice-activated control system. The voice-activated control system uses a microprocessor to analyze the voice commands and compares them to predetermined commands in the device's computer memory bank. The computer then transmits digital instructions through the device's communications network to the alarm. When the user wishes to voice-activate the alarm, the user can press the VOICE ACTIVATION key and say SET TIMER by talking into the device through a microphone 22, speaking in a normal voice. The system can recognize accents and dialects of the English language and can be enabled to recognize commands in any language including, for example, Spanish and French. The LANGUAGE RESET key 54 allows the user to change the language on the display screens and the voice-activating language from, for example, English to Spanish and vice versa.

When the user presses the VOICE ACTIVATION key, a chime can be heard. After the chime, the user can tell the device a command. When the user gives a command, the voice repeats the command over the speaker. For example, the user can speak into the microphone 22 and say SET TIMER", the device 2 repeats the command, then the user states the letter of the event key 6, and the device 2 repeats the letter of the event key. The user then designates the name of the event represented by the event key and the time to alarm, for example, the user says "HEART PILL, TWO HOURS." The system repeats the command "HEART PILL, TWO HOURS," and sets the timer for two hours. To cancel the command, the user can say "CANCEL TIMER." When two hours have elapsed, the device audibly emits the phrase "H" "HEART PILL" until the user deactivates the alarm by pressing the ALARM key 60. The voice-activated control system activates an alarm such that, at an alarm point, which is displayed on the third display screen 68, a recorded voice plays back the recorded event. The recorded event is repeatedly played back until the user deactivates the system. The time of the alarm will blink in the third display screen 68, so that the user can compare the alarm time with the current time shown in second display screen 14 to see how much time has elapsed.

The following are examples of how a user can (1) record medical events such as symptoms; (2) record a medical event regarding intake of a medication; (3) set the alarm to remind the user to take a specific medication or medications at the alarm time(s); (4) schedule a predetermined time between specific medications; and (5) set a voice-activated control system to alarm to remind the user to take a specific medication or medications at the alarm time(s).

EXAMPLE 1

Figure 5B:
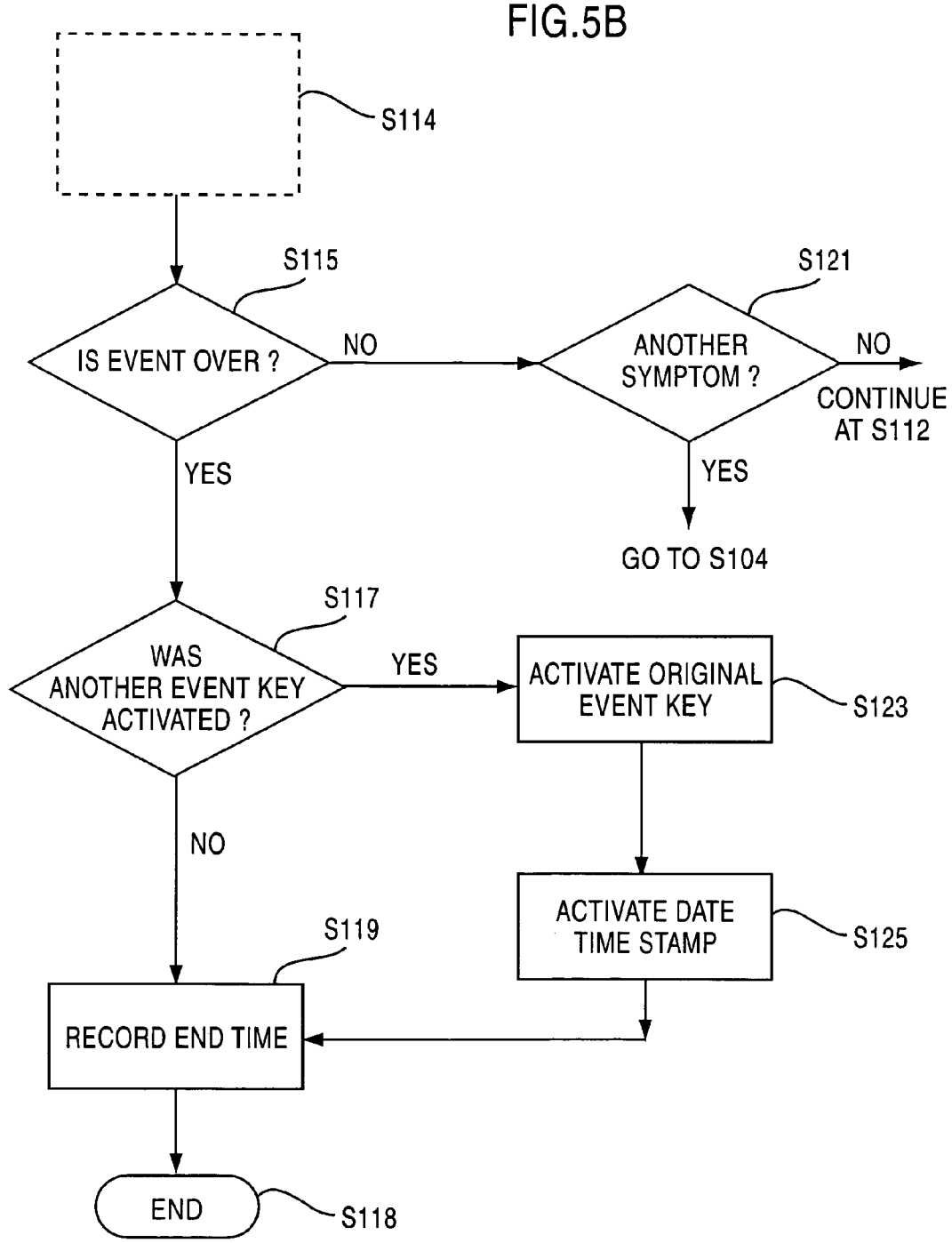

FIGS. 5A and 5B illustrate a flow chart for a method of recording unscheduled medical events in the device 2 according to one embodiment of the present invention. To record medical events, such as symptoms, the user can start the device, which includes turning on the device with the ON key 50. At step S102, the user can assign the event keys. As shown in FIG. 1, the event keys B to G, and I to K can be assigned with possible symptoms. The user can press any one of the event keys 6 associated with the identified symptoms at step S104. For example, the user can press event key "C" to begin recording that an elbow pain is being felt. At step S106, the user rates the severity of the elbow pain by choosing one of the rating keys 12. The user can choose to not rate the severity and continue the entries by pressing the DATE AND TIME key at step S116. The elbow pain will be recorded with the date and time that it occurred. If the user chooses to rate the severity, at step S108, the user can press one of rating keys 12, which are numbered 1 to 10. Rating key number "1" can represent a symptom that is least severe, and rating key number "10" can represent a symptom that is most severe. The user can press rating key "5" to indicate that the elbow pain is moderate. The user can then complete the recordation of the elbow pain by pressing the DATE AND TIME key at step S110, thereby recording the specific date and time that the user felt a moderately severe elbow pain. If the user chooses to record how long the elbow pain is being felt at step S112, the user can record the beginning time of the pain at step S114, by pressing the BEGIN key 36a at the time that the elbow pain is first felt, and pressing the END key 36b when the elbow pain stops, thereby, recording the beginning and ending of the elbow pain. If a user records a second event after pressing the BEGIN key 36a for the first event, in order to record the END key 36b of that first event, the user must press the original or first event key 6 and the DATE AND TIME key 18 again before pressing the END key 36b at S118.

If the user has additional symptoms, such as, for example, trouble breathing, which is assigned to event key "J", the user can start recording information related to the symptom at S104, as discussed above. For example, when the first symptom (elbow pain) that is being recorded ends, as indicated at step S115, but a second symptom (trouble breathing) is being concurrently recorded as indicated at step S117, the user can designate the END key 36b for the elbow pain by pressing the event key "C" at step S123, then the DATE AND TIME key at step S125, followed by the END key 36b at step S119. The display screen 4 will show the time that the END key 36b was pressed for the elbow pain. The display screen 4 can also show the time difference between the beginning and ending of the elbow pain in hours, minutes, and seconds.

EXAMPLE 2

To record a medical event regarding the intake of a medication, the user can assign an event key with an event key identifier 10, press the event key 6, and then press the DATE AND TIME key 18. For example, as shown in FIG. 1, the event key "H" has been assigned with the event key identifier "HEART PILL". The flow chart of FIG. 5A shows that the user assigns an event key at step S102, then activates an event key at step S104 by pressing event key "H" followed by the DATE AND TIME key 18 at step S116 to record that the user is taking the heart pill on a specific day at a specific time. To later display that event, in order to see at what time the medication was taken, the user can press the event key, "H," and then the Display bar. If there have been multiple recordings of this event, the user may be required to use the scroll bar 52.

EXAMPLE 3

To set the alarm to remind the user to take a specific medication or medications at the alarm time, the user can assign an event key or keys 6 with an event key identifier or identifiers 10 as at step S122 in FIG. 6. For example, as shown in FIG. 1, the event key "H" has been assigned with the event key identifier "HEART PILL" and the event key "L" has been assigned with the event key identifier "STATIN."

The user can then set a timer by pressing the SET TIMER key 16 at step S124. Pressing the SET TIMER key 16 clears the current date and time from the second display screen 14. To set the timer, the user can press the HOURS, MINUTES and SECONDS keys 62a, 62b, 62c, respectively, to adjust the hours and/or minutes/and/or seconds that will elapse before the alarm signal is generated. The hours and minutes and seconds will be displayed in the second display screen 14 as they are being set. At step S126, the user enters the medication that is, or medications that are, being timed. The user can then press the START KEY 16b, followed by the ALARM key 60 at S132 to start the timer that counts down the time until the medication or medications can or must be taken. The clock reverts to displaying the current date and time when the alarm is set. The alarm time will display in third display screen 68.

At step S134 the device will generate an audible alarm signal. The user can stop the timer before the alarm time is reached by pressing the STOP key 16b and reset the timer by pressing the RESET key 16c.

Manually, if the user would like to time how long to hold his or her breath after administering an inhalation aerosol, for example, the user may press SET TIMER, press the SECONDS key 62c to set the desired number of seconds, press the START KEY 16b, and when the desired time has elapsed, press the STOP key 16a, and RESET 16c.

EXAMPLE 4

As shown in FIG. 6, the user can schedule a predetermined time between different medications, beginning at step S122, where the user assigns event keys 6 with event key identifiers 10. At step S124, the user can set the timer 16 to establish the time to take a first medication. At step S126, the user can enter the first medication. The user can begin storing information for the second medication by entering a predetermined time interval at step S128 and the medication that requires the predetermined time interval at step 126. The user can choose to enter more medications at step S130. The steps S130, S126, and S128 repeat until there are no more medications to enter. This can continue until all medications are scheduled, at which point, the user can press ALARM at S132. At step S134, the device 2 will issue an alarm signal through the speaker 20.

For example, as shown in FIG. 1, event key "A" is assigned the event key identifier "ANTACID" and event key "H" is assigned the event key identifier "HEART PILL" and event key "L" is assigned the event key identifier "STATIN." If the user needs to maintain at least two hours between the antacid and the heart pill, the user can press the SET TIMER key 16 at step S124. The second display screen 14 will change from displaying the current date and time to displaying a blank screen for the user to enter a time for taking the first medication. The user can set the alarm for the heart pill by pressing the HOURS and MINUTES keys 62a, 62b until the display screen 14 reads two hours. The user can then press event key "H" to represent that the heart pill is to be taken in two hours. The time of this alarm can be shown in the third display screen 68.

If the user is scheduled to take a statin pill four hours after the heart pill, the user can enter a second predetermined time, for example four hours, at step S128, and then press the event key "L". If there are no further medications to schedule, the user sets the alarm at step S132. At step S134, the device 2 will issue an alarm signal through the speaker 20 after two hours, and then four hours after that. At two hours, the letter "H" in the display screen 4 can blink until deactivated, and four hours later, the letter "L" can blink until deactivated. The time of the alarm will blink in the third display screen 68, so that the user can compare the alarm time with the current time shown in the second display screen 14 to see how much time has elapsed.

In one embodiment of the present invention, multiple medications that can be taken at the same time can be entered together at step S126, while later medications that can be taken together can be entered at step S126.

EXAMPLE 5

The voice-activation feature of the present invention allows the user to activate the commands in the device by voice. For example, the user can schedule a time to take one medication or set a predetermined time interval between different medications with voice commands.

For timing the taking of one medication, beginning at step S122, the user assigns event keys 6 with event key identifiers 10. At step S124, the user can set the timer 16 to establish the time to take the first medication. To set the timer, the user can press the VOICE ACTIVATION key 58. When the user presses the VOICE ACTIVATION key, a chime can be heard. After the chime, the user says "SET TIMER" thereby activating the SET TIMER key 16. When the user says "SET TIMER, the voice repeats "SET TIMER" over the speaker. Then the user states the letter of the event key 6, for example, "H" and the device 2 repeats the letter "H". The second display screen 14 will change from displaying the current date and time to displaying a blank screen for the user to state the hours and/or minutes for which the timer will be set. The user can then orally state the first medication and the time until the first medication will be taken. The user then designates the name of the event represented by the event key and the time to alarm. For example, the user says "HEART PILL, TWO HOURS." The system repeats the command "HEART PILL, TWO HOURS," and sets the timer for two hours. When two hours have elapsed, the device audibly emits the phrase "H" "HEART PILL" until the user deactivates the alarm. The user can deactivate the alarm by pressing the ALARM key 60 or saying, "deactivate alarm". The voice-activated control system activates an alarm such that, at an alarm point, which is displayed on the third display screen 68, the recorded voice plays back the recorded event. The recorded event is repeatedly played back until the user deactivates the system. The "H" in the display screen 4 also blinks at the alarm point until deactivated. The time of the alarm will blink in the third display screen 68, so that the user can compare the alarm time with the current time shown in the second display screen 14 to see how much time has elapsed.

For timing the taking of multiple medications, beginning at step S122, the user assigns event keys with event key identifiers. At step S124, the user can set the timer 16 to establish the time to take the first medication. To set the timer, the user can press the VOICE ACTIVATION key 58, and say "SET TIMER" thereby activating the SET TIMER key 16. The second display screen 14 will change from displaying the current date and time to displaying a blank screen for the user to state the hours and/or minutes for which the timer will be set. The user at step S126 can then orally state the first medication and at step 128 the time between the first and second medication. At step S130 the user indicates whether there are more medications to be taken. At step S126, the user can orally state the second medication to be taken. The steps S130, S126, and S128 continue until there are no more medications to enter.

For example, as shown in FIG. 1, event key "A" is physically assigned the event key identifier "ANTACID" and event key "H" is physically assigned the event key identifier "HEART PILL". However, the user can also assign the event key with voice-recorded event key identifiers of the medications at step S122. To assign the voice-recorded event key identifiers, the user can press the VOICE ACTIVATION key 58, then press the event key 6, and speak the name of the medication into the microphone 22. The device 2 through the speaker 20 can play back the event key identifier with an audible "A" and the name of the medication recorded in the system.

After the event keys are assigned, if the user needs to maintain at least two hours between the antacid and the heart pill, the user can say "SET TIMER" at step S124 to activate the SET TIMER key 16. If the user has just taken an antacid, the user can then say "HEART PILL" "TWO HOURS" and the system can audibly play back "HEART PILL" "TWO HOURS". If the user is scheduled to take a STATIN pill four hours after the heart pill, the user will then say "STATIN PILL" FOUR HOURS." If there are no further medications to schedule, the user then says ALARM at step S132. At step S134, the device 2 will issue an alarm signal through the speaker 20, two hours, and four hours after that.

The system can audibly play back the recording "ANTACID"; then, two hours later, "HEART PILL"; and four hours later, "STATIN". To turn off the alarm, the user can the STOP key 16b and reset the timer by pressing the RESET key 16c.

In another embodiment of the present invention, the user can be prompted by the display screen to enter the information to be recorded and played back. Further, the device of the present invention can include a timing sequence to calculate the difference between the begin and end times of the medical events. For example, the BEGIN key 36a and the END key 36b can be programmed to being and end a time sequence and calculate the duration of the event.

As discussed above, the device of the present invention can incorporate the features of PDAs such as icon keys that are displayed on the display screen. In this embodiment, the device 2 includes a stylus pen 34, so that the user can select the event key 6, rating key 12, set the timer, the alarm, record a medical event and schedule a predetermined time between medical events as disclosed above, through the display screen 4. PDAs on the market include, for example, the iPAQ manufactured by Hewlett Packard, the Palm series manufactured by palmOne, Inc. and the Pocket PC series manufactured by Dell Inc.

The electronic memory device of the present invention can also include a backlight that illuminates the display screens 4, event 6 and rating keys 12, when any of the keys on the keypad are pressed.

Figure 3:
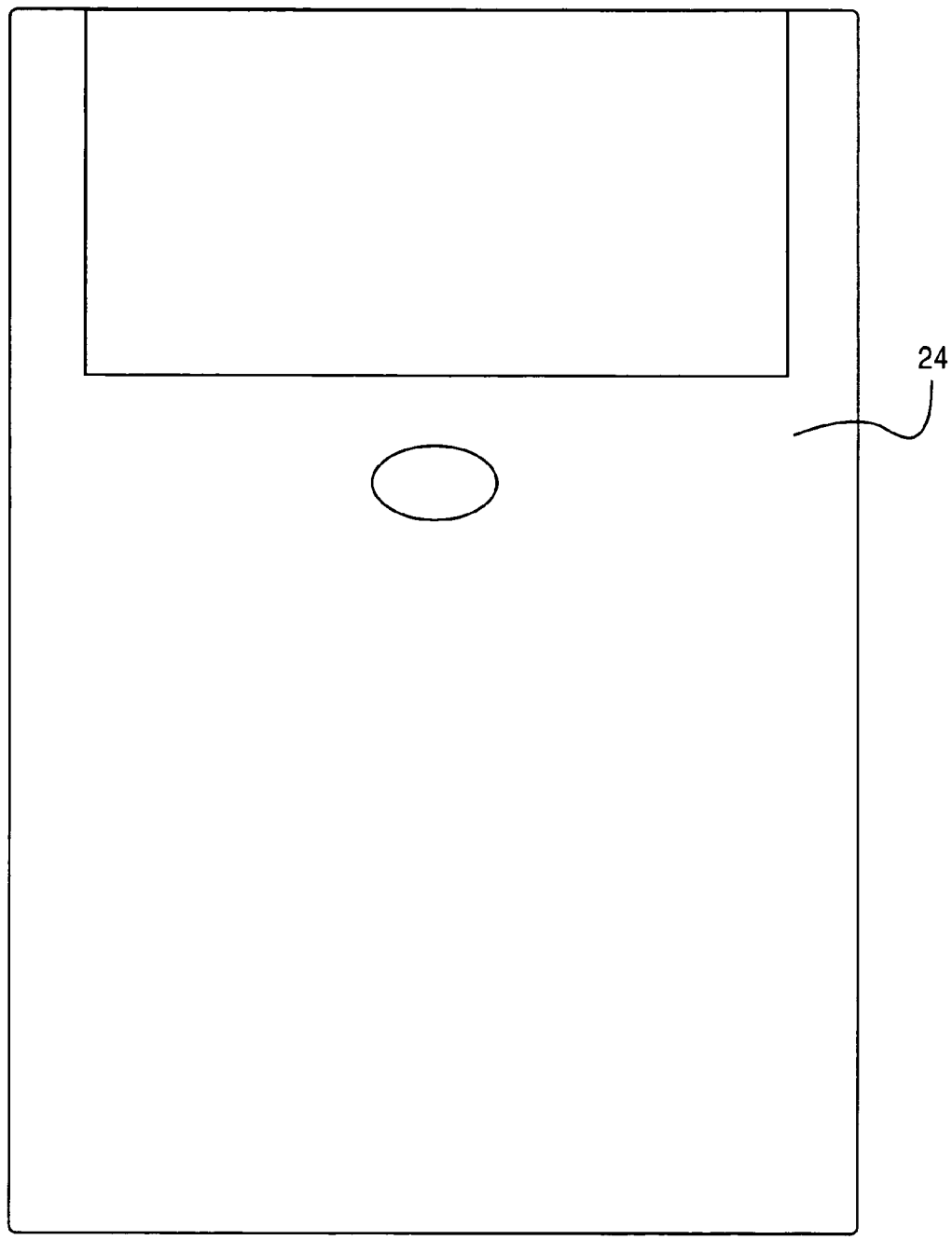
FIG. 3 illustrates a rear view of the electronic memory pad according to one embodiment of the present invention.

As shown in FIG. 3, the device can also include a rechargeable battery 24 similar to that in a cellular telephone.

Figure 4:
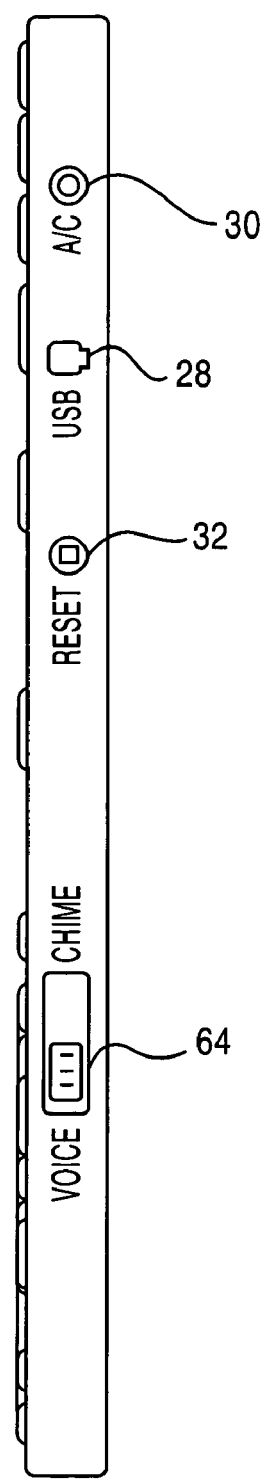
FIG. 4 illustrates a side view of the electronic memory pad according to one embodiment of the present invention.

As shown in FIG. 4, the device can further include a universal serial bus (USB) port 28 for uploading recorded information into a personal computer, and an A/C port 30 for inserting an adapter to charge the battery 24. A system-reset button 32 can be provided to clear the system of all the stored information in the device 2. The reset button 32 includes a recessed portion in the side of the device to prevent accidental activation. A small narrow object carefully targeted to the recessed portion can access the recess button.

Figure 7:
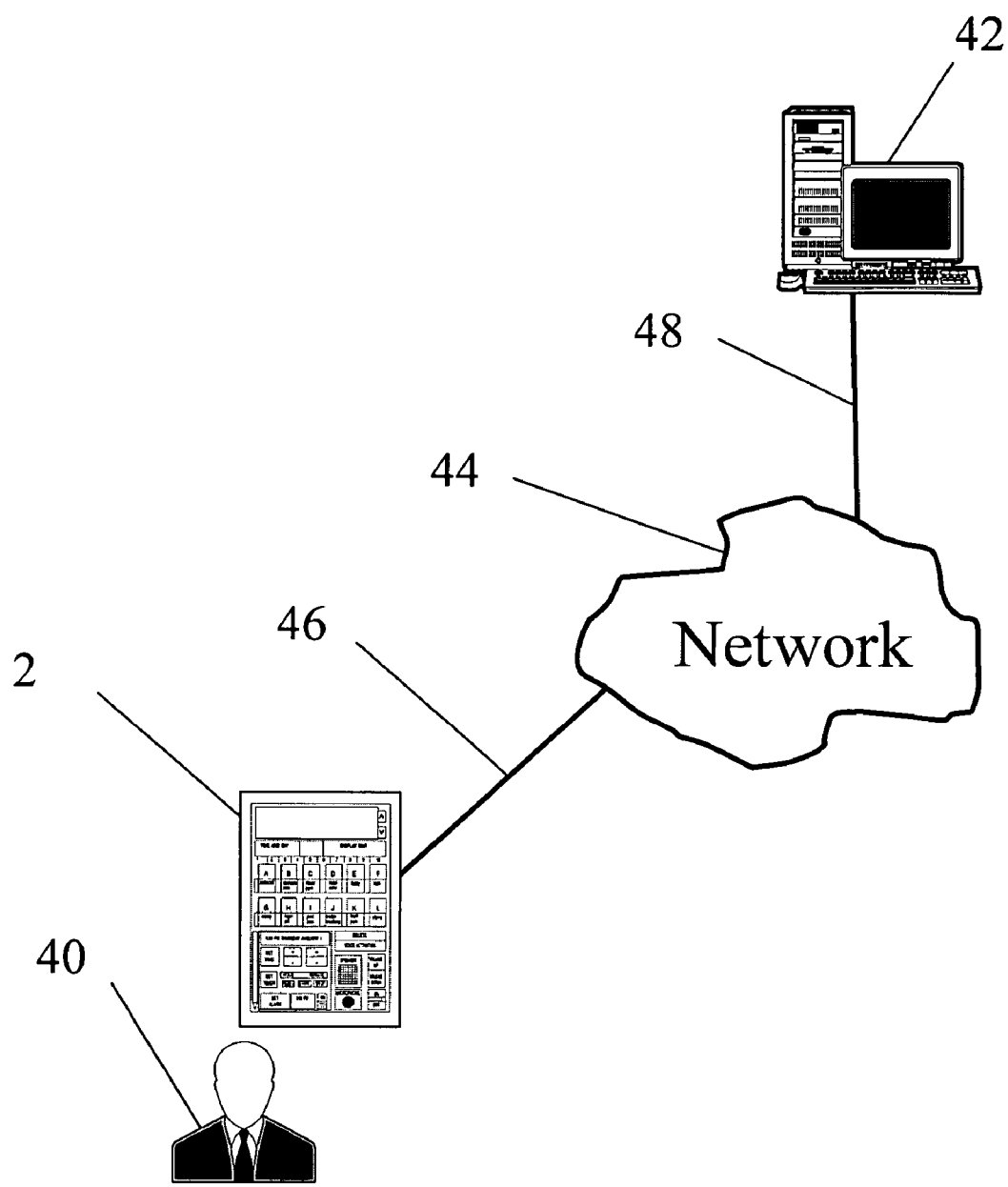
FIG. 7 illustrates a system in which data from the device of the present invention can be uploaded.

The method and system of the present invention operate in a stand-alone environment, such as in a single terminal, that is, the device 2. However, as shown in FIG. 7, in an embodiment of the present invention, some data for use in the system is, for example, input by a user 40 via a terminal, such as the electronic memory device 2 of the present invention, coupled to a server 42, such as a PC, minicomputer, mainframe computer, microcomputer, or other device having a processor and a repository for data and/or connection to a processor and/or repository for data, via, for example, a network 44, such as the Internet or an intranet, and couplings 46, 48. The couplings 46, 48 include, for example, wired, wireless, or fiberoptic links.

While the examples of the present invention are disclosed with respect to the medical field, the features of the present invention are equally applicable for timing sequences with respect to exercise routines or other physical activities.

Example embodiments of the present invention have now been described in accordance with the above advantages. It will be appreciated that these examples are merely illustrative of the invention. Many variations and modifications will be apparent to those skilled in the art.

I claim:

1. An electronic memory device comprising:
   a first display screen;
   a keypad having a plurality of event keys designating events to be recorded in the device and to be displayed on the first display screen, the plurality of event keys being interchangeably assigned an event;
   a plurality of rating keys for recording and rating each of the events;
   a memory circuit wherein a record of all events is recorded for storage and playback;
   a time-comparison circuit for comparing a present time with an alarm time;
   an alarm signal for generating an audible alarm at the alarm time,
   a voice-activated control system that records and plays back voice-command information; and
   a second display screen for displaying a current date and time.

2. The electronic memory device according to claim 1, wherein the event comprises a medical event.

3. The electronic memory device according to claim 2, wherein the medical event comprises a physical symptom.

4. The electronic memory device according to claim 2, wherein the medical event comprises taking a medication.

5. The electronic memory device according to claim 1, further comprising a plurality of event key identifiers for customizing the plurality of event keys.

6. The electronic memory device according to claim 5, wherein the plurality of event key identifiers comprises adhesive labels.

7. The electronic memory device according to claim 5, wherein the event key identifiers comprise labels describing a medical event.

8. The electronic memory device according to claim 1, wherein the time comparison circuit includes a timer for setting a predetermined time interval between events.

9. The electronic memory device according to claim 1, further comprising a backlight that illuminates the first display screen and the keypad when any of the keys on the keypad are pressed.

10. The electronic memory device according to claim 1, wherein the plurality of event keys comprise icon keys on the first display screen.

11. The electronic memory device according to claim 10, further comprising a stylus pen for selecting any of the icon keys.

12. The electronic memory device according to claim 1, wherein the first display screen comprises an LCD.

13. The electronic memory device according to claim 1, further comprising a timer for recording the duration of the event.

14. The electronic memory device according to claim 1, further comprising a microphone and a speaker.

15. The electronic memory device according to claim 1, wherein the device comprises a personal digital assistant-based memory circuit and time-comparison circuit.

16. The electronic memory device according to claim 1, wherein the device further comprises personal digital assistant-based icon buttons.

17. The electronic memory device according to claim 1, wherein the second display screen displays a current date and time while the first display screen displays events to be recorded in the device.

18. A method of recording an event in an electronic memory device, the method comprising:
   assigning a plurality of event keys with event key identifiers;
   activating one of the plurality of event keys to display an event on a display screen;
   activating a DATE AND TIME key to display and record a current date and time on the display screen; and
   activating a BEGIN key to begin recording a duration of the event and an END key to conclude recording.

19. The method according to claim 18, wherein the at least one event comprises a medical event.

20. The method according to claim 19, further comprising rating the medical event.

21. The method according to claim 18, wherein the step of assigning comprises assigning customized labels to the plurality of event keys.

22. The method according to claim 18, wherein the step of recording the duration of the event comprises indicating a begin and end time of the event.

23. A method of scheduling a predetermined time interval between medical events in an electronic memory device having at least one display screen, a plurality of event keys, a memory circuit, and a time-comparison circuit, the method comprising:
   assigning different medical events to different ones of the plurality of event keys;
   storing a plurality of predetermined time intervals between the different medical events;
   activating the time-comparison circuit for comparing a present time with a predetermined time for each of the plurality of predetermined time intervals;
   issuing an alarm after each of the plurality of predetermined time intervals; and
   displaying the event key in the at least one display screen at the issuance of the alarm.

24. The method according to claim 23, wherein the step of assigning comprises assigning customized labels to the plurality of event keys.

25. The method according to claim 23, wherein the step of activating the time comparison circuit comprises voice-activating a start and stop time of the time-comparison circuit.

26. A method of establishing a predetermined time interval in an electronic memory device having a voice activated control system, the method comprising:
- receiving a voice activated command through the voice activated control system;
- activating a time comparison circuit to start a timer;
- comparing a current time to a predetermined time until the predetermined time is reached;
- issuing an audible alarm at the predetermined time; and
- displaying the predetermined time on a display screen, wherein the display screen displays the time that has elapsed since the alarm began.

27. The method according to claim 26, wherein the audible alarm continues at predetermined intervals until deactivated.

* * * * *